(12) United States Patent
Pagoria et al.

(10) Patent No.: US 8,815,606 B2
(45) Date of Patent: Aug. 26, 2014

(54) THIN-LAYER CHROMATOGRAPHY AND COLORIMETRIC ANALYSIS OF MULTI-COMPONENT EXPLOSIVE MIXTURES

(75) Inventors: Philip F. Pagoria, Livermore, CA (US); Alexander R. Mitchell, Livermore, CA (US); Richard E. Whipple, Livermore, CA (US); M. Leslie Carman, San Ramon, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 744 days.

(21) Appl. No.: 12/106,400

(22) Filed: Apr. 21, 2008

(65) Prior Publication Data

US 2009/0221085 A1 Sep. 3, 2009

Related U.S. Application Data

(60) Provisional application No. 60/930,781, filed on May 17, 2007.

(51) Int. Cl.
*G01N 30/90* (2006.01)
*G01N 30/96* (2006.01)

(52) U.S. Cl.
USPC .......... 436/162; 436/164; 436/166; 436/169; 436/172; 436/174

(58) Field of Classification Search
USPC .............. 436/162, 161; 210/635, 656, 198.2, 210/658; 73/53.01; 530/413, 417
See application file for complete search history.

(56) References Cited

U.S. PATENT DOCUMENTS

| | | | |
|---|---|---|---|
| 4,313,906 A * | 2/1982 | Filipi et al. ................ | 422/69 |
| 4,372,850 A * | 2/1983 | Okumura et al. ......... | 210/198.3 |
| 6,096,205 A | 8/2000 | Haas et al. | |
| 6,420,181 B1 * | 7/2002 | Novak .................... | 436/104 |
| 6,454,939 B1 * | 9/2002 | Haas et al. .............. | 210/198.3 |
| 6,787,366 B1 * | 9/2004 | Novak .................... | 436/162 |
| 2005/0064601 A1 | 3/2005 | Haas et al. | |
| 2005/0287036 A1 | 12/2005 | Eckels et al. | |

OTHER PUBLICATIONS

Yinon, J., Analysis of Explosives, 1977, Chemical Rubber Co. Cleveland, 7, 1, 1-35.*
UVIC, Thin Layer Chromatography, 2005, websited accessed Sep. 15, 2009, http://web.uvic.ca/~berryde/techniques/tlc.pdf.*

(Continued)

*Primary Examiner* — Allison Gionta Fitzsimmons
(74) *Attorney, Agent, or Firm* — Eddie E. Scott

(57) ABSTRACT

A thin-layer chromatography method for detection and identification of common military and peroxide explosives in samples includes the steps of provide a reverse-phase thin-layer chromatography plate; prepare the plate by marking spots on which to deposit the samples by touching the plate with a marker; spot one micro liter of a first standard onto one of the spots, spot one micro liter of a second standard onto another of the spots, and spot samples onto other of spots producing a spotted plate; add eluent to a developing chamber; add the spotted plate to the developing chamber; remove the spotted plate from the developing chamber producing a developed plate; place the developed plate in an ultraviolet light box; add a visualization agent to a dip tank; dip the developed plate in the dip tank and remove the developed plate quickly; and detect explosives by viewing said developed plate.

23 Claims, 2 Drawing Sheets

(56) References Cited

OTHER PUBLICATIONS

Fried, B., Sherma, J., Handbook of Thin-Layer Chromatography: Basic TLC techniques, Materials, and Apparatus, 2003, Marcel Dekker, 3rd Edition, 1-20.*
Wall, P. E., Thin-Layer Chromatography: A Modern Practical Approach, Development Techniques, 2005, 86-99.*
Sherma, J., Analytical Instrumentation Handbook, Chromatogram Development, 2005, Marcel Dekker, 3rd Edition.*
Sherma, J., Encyclopedia of Chromatography, 2001, Taylor & Francis Group, Detection (Visualization) of TLC Zones, 2nd Edition, vol. 1, pp. 249-252.*
P. D. Shaw et al., Detecting and characterizing N-acylc-homoserine lactone signal molecules by thin-layer chromatography, Jun. 1997, Proc. Natl. Acad. Sci. USA, vol. 94, p. 6036-6041.*
J. Yinon; S. Zitrin; Modern Methods and Applications in Analysis of Explosives, 1993, John Wiley & Sons ltd, pp. 33-41.*
L. Haag, The CAC News, Black Powder Substitutes: Their Physical and Chemcal Properties and Performance, 2001, Third Quarter, Pages cover—41.*
Bochner, B. R., Ames, B. N., Complete Analysis of Cellular Nucleotides by Two-dimensional Thin Layer Chromatography, 1982, Journal of Biological Chemistry, vol. 257, No. 16, Issue of Aug. 25, pp. 9759-9769.*
J.R. Mohrig; C. N. Hammond; P.F. Schatz; Part 2: Chromatography Visualization Reagents, 2006, 2nd Edition, pp. 146-183.*
J. Sherma, Basic TLC Techniques, Materials, and Apparauts, Handbook of Thin-Layer Chromatography, 2003, Taylor & Francis Group LLC.*
Stillway, B., Pettus, B., Lipid Analysis of Cultured Cells by Thin-Layer Chromatography (TLC), 2003, MUSC Department of Biology & Molecular Biology.*
Thin Layer Chromatography (TLC) Guide, 2005, MIT, website accessed Sep. 21, 2009 http://ocw.mit.edu/NR/rdonlyres/Chemistry/5-301January--IAP-2004/1469AB39-E020-43F8-BE06-2D6B12071E13/0/8_3_tlc.pdf.*
Royds et al., A case study in forensic chemistry: The Bali bombings, 2005, Talanta, 67, pp. 262-268.*

* cited by examiner

THIN-LAYER CHROMATOGRAPHY AND COLORIMETRIC ANALYSIS OF MULTI-COMPONENT EXPLOSIVE MIXTURES

CROSS-REFERENCE TO RELATED APPLICATIONS

This application claims the benefit of U.S. Provisional Patent Application No. 60/930,781 filed May 17, 2007 and titled "Quick and Accurate Analysis of Multi-component Explosive Mixtures by a Combination of Thin-layer Chromatography and Colorimetric Techniques." U.S. Provisional Patent Application No. 60/930,781 filed May 17, 2007 and titled "Quick and Accurate Analysis of Multi-component Explosive Mixtures by a Combination of Thin-layer Chromatography and Colorimetric Techniques" is incorporated herein by this reference.

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to detection and identification of explosives and more particularly to a thin-layer chromatography method for detection and identification of explosives.

2. State of Technology

U.S. Pat. No. 6,096,205 for a hand portable thin-layer chromatography system provides the following state of the art information: "Various analytical techniques are used to measure the type and amount of contamination from unknown chemicals in environmental, industrial, civilian, and military situations. Conventional thin-layer chromatography (TLC) analysis is routinely used in analytical laboratories worldwide for quantitative and qualitative characterization of unknowns. This technique is ideal for rapid pre-screening and identification of known and unknown chemicals. TLC allows multiple samples and standards (in mg to ng quantities) to be chromatographed simultaneously on a TLC plate in a solvent tank. Semiquantitative and qualitative assessment from all samples is then readily obtained by inspection of the plates, which may be chemically developed and then illuminated to display the separated components (appearing as spots). Further quantitative analysis may be performed using an illumination box, camera, and data acquisition equipment. Unfortunately, conventional TLC apparatus is cumbersome, typically made of glass, and is not field-deployable or field-ruggedized for on-site analysis. Current TLC hardware is not hand portable when including all the necessary support equipment such as plates, tanks, solvent pipettes, rulers etc. Furthermore, the illumination and data acquisition equipment needed to fully analyze samples is oversized and extremely heavy. Thus, there is a need for a hand portable, field-ready TLC system, including data acquisition capability, that is cost-effective and efficient for analyzing multiple samples of unknown chemicals on-site in a variety of emergency and non-emergency situations."

United States Published Patent Application No. 2005/0064601 for a system for analysis of explosives provides the following state of the art information: "A system for analysis of explosives. Samples are spotted on a thin layer chromatography plate. Multi-component explosives standards are spotted on the thin layer chromatography plate. The thin layer chromatography plate is dipped in a solvent mixture and chromatography is allowed to proceed. The thin layer chromatography plate is dipped in reagent 1. The thin layer chromatography plate is heated. The thin layer chromatography plate is dipped in reagent 2."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a thin-layer chromatography method for detection and identification of common military and peroxide explosives in samples. The method includes the steps of provide a reverse-phase thin-layer chromatography plate; prepare the plate by marking spots on which to deposit the samples by touching the plate with a marker; spot one micro liter of a first standard onto one of the spots, spot one micro liter of a second standard onto another of the spots, and spot samples onto other of the spots producing a spotted plate; add eluent to a developing chamber; add the spotted plate to the developing chamber; remove the spotted plate from the developing chamber producing a developed plate; place the developed plate in an ultraviolet light box; add a visualization agent to a dip tank; dip the developed plate in the dip tank and remove the developed plate quickly; and detect explosives by viewing said developed plate.

A modular field portable thin-layer chromatography (TLC) kit for the detection and identification of common military, peroxide and commercial-type fuel/oxidizer explosives containing modules divided into three categories: military and peroxide explosives, inorganic explosives (oxidizers) and urea nitrate (UN) containing explosives. The kit uses reverse-phase C18 TLC plates (RBP-18) to identify both common military explosives (HMX, RDX, Tetryl, Explosive D, picric acid, CL-20, TNT, NG, and PETN) and peroxide explosives (TATP and HMTD) all on the same plate. The method provides confirmation of the identity of a suspected explosive without changing the identity of the TLC plate.

The TLC kit also contains a module for the separation and detection of inorganic oxidizing anions such as nitrate, perchlorate, chlorate bromate and nitrite that are typically used in fuel/oxidizer explosive mixtures (e.g., potassium chlorate/sugar). Applicants' anion methodology employs HPTLC cellulose plates and 2,6-dichloroindophenol as the calorimetric reagent and gives a good separation of the anions. A module was also developed for the separation and detection of urea nitrate (UN) containing explosives. Applicants' urea methodology uses RP-18W plates and dimethylaminobenzaldehyde as the as the colorimetric reagent.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
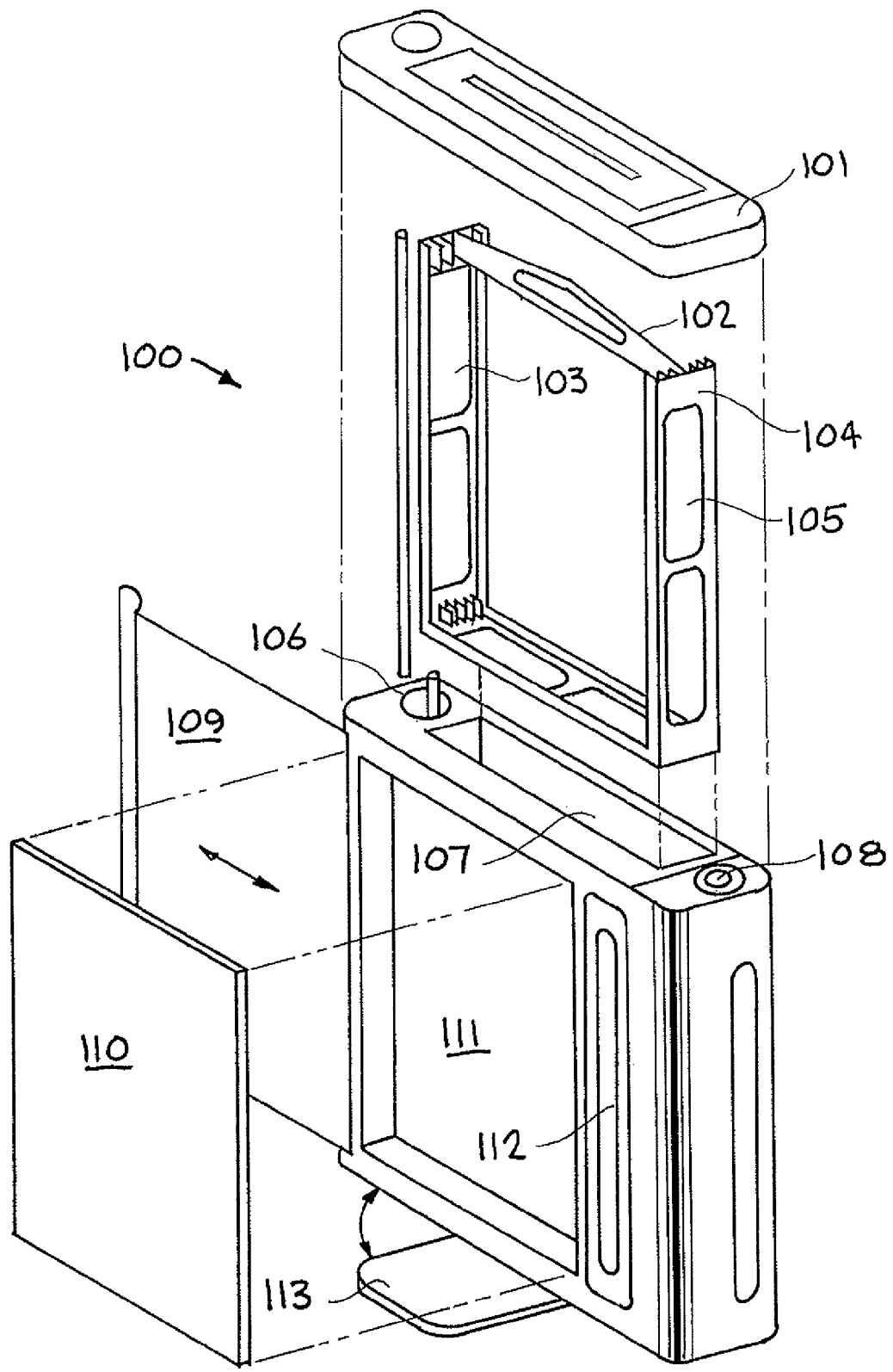
FIG. 1 illustrates an embodiment of a hand portable thin-layer chromatography (TLC) system field-deployable for on-site analysis.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, an embodiment of a system for analysis of explosives that is a hand portable thin-layer chromatography (TLC) system field-deployable for on-site analysis is illustrated. This embodiment of a system for analysis of explosives is designated generally by the reference numeral 100. The system 100 is a Thin-Layer Chromatography (TLC) system. TLC is a technique that is used to judge the purity of a synthesized compound or to indicate the extent of progress of a chemical reaction. In TLC, a small quantity of a solution of the mixture to be analyzed is deposited as a small spot on a TLC plate.

The small tank reservoir 107 eliminates the need for a saturation pad. A mere 10 mL of solvent can be used to process over 100 samples. The solvent can be stored in a container which fits into one of the storage chambers 108. Pipettes can be stored in another chamber 106. A tool chamber 111 at the front of the unit holds extra TLC plates; in one embodiment, a sliding door 109 that clips in place provides access to the TLC plates 10. The TLC unit has a window 112 for visually monitoring the solvent level during the TLC plate processing.

The holder basket 104 fits into the solvent tank 107, and the basket 104 accommodates a convenient number of TLC plates (e.g., six) for processing. The basket 104 has a unitary body comprising two parallel sides and a bottom portion, is designed to prevent aberrant wicking along the TLC plate edges, which causes the separated components of the multiple samples on the TLC plate to be unevenly distributed across the top of the plate. To prevent this effect, the sides (and bottom) of the basket 104 have openings 105 so that the TLC plates do not touch the sides during processing in the solvent. This design provides superior chromatographic separation of the components. Grooves or separators at the top and bottom of the basket 104 prevent the TLC plates from touching one another. The basket 104 has a handle 102 to facilitate the transfer of the basket 104 in and out of the solvent tank 107.

The TLC unit also features a foot (or feet) 113 that swings out from the bottom of the unit to provide additional stability. A lid 101 for covering the unit is gasket-sealed and can be screwed down for better solvent equilibration.

The present invention provides a new field portable thin-layer chromatography (TLC) kit for the detection and identification of common military, peroxide and commercial-type fuel/oxidizer explosives. It is a modular unit with modules designed specifically for certain types of explosive compounds. The kit is useful to the military, law enforcement and first responders. The modules are divided into three categories: military and peroxide explosives, inorganic explosives (oxidizers) and urea nitrate (UN) containing explosives.

The present invention includes uses of reverse-phase C18 TLC plates (RP-18) to identify both common military explosives (HMX, RDX, Tetryl, Explosive D, picric acid, CL-20, TNT, NG, and PETN) and peroxide explosives (TATP and HMTD) all on one plate. The C18 TLC plate was found to be superior to the regular phase silica gel plates. The use of the reverse phase plates also has the advantage of being able to change the elution solvent to produce a different separation pattern. This provides a method to confirm the identity of a suspected explosive without changing the identity of the TLC plate. This is important when there may be a non-explosive material that has the same retention factor ($R_f$) as one of the standard explosive compounds. A second elution solvent would allow confirmatory evidence that the suspected spot on the TLC plate is indeed the explosive in question. The use of the colorimetric reagent, diphenylbenzidine, when applied to the RP-18 TLC plates allows colorimetric confirmation of the identity of the suspect explosives.

The present invention also contains a module for the separation and detection of inorganic oxidizing anions such as nitrate, perchlorate, chlorate, bromate and nitrite which are typically used in fuel/oxidizer explosives (e.g., potassium chlorate/sugar). Our anion methodology employs HPTLC cellulose plates and 2,6-dichloroindophenol as the calorimetric reagent and gives a good separation of the anions. A module has been developed for the separation and detection of urea nitrate (UN) containing explosives. Applicants' urea methodology uses RP-18W plates and dimethylaminobenzaldehyde as the colorimetric reagent. This technology allows the first responders and law enforcement officials to assess whether a suspected item contains one these explosive ingredients.

The present invention has use in the identification of explosives for law enforcement, military and forensic applications. The present invention has use in the separation and identification of known and unknown explosives and their components for military applications including unexploded ordnance, suspect explosive components, pipe bombs, and IED's.

Applicants' invention provides a thin-layer chromatography (TLC) system for the detection and identification of common military, peroxide and commercial-type fuel/oxidizer explosives. Applicants' invention provides a C18 TLC separation methodology that allows reproducible separation and identification of the explosive standards. It involves spotting explosive unknowns and authentic samples onto the C18 TLC plate and developing the TLC plate with a 16:1 toluene/propan-2-ol mixture (takes around 15 minutes). The plate is dried and exposed to 254 nm UV light. The nitroaromatic and nitramine explosives show up as dark spots on a greenish background. The plate is then dipped into the 0.02% diphenylbenzidine/EtOH solution. After removing the plate and drying, TATP and HMTD show up as blue spots. The plate is then irradiated with 254 nm UV light for a few minutes and the nitrate esters show up as dark spots on a light blue background. This procedure not only identifies all the explosives mentioned but it also allows the user to separate the suspected compounds by their explosive class, i.e. nitramines, nitroaromatic, peroxides or nitrate esters. A different elution solvent may also be used with this plate. When a water/MeOH/acetonitrile solvent mixture is used as the eluant the explosives reverse their order of $R_f$ and Explosive D now has the highest $R_f$ value. By using these two elution solvents, 16:1 toluene/propan-2-ol and a 11:9:2 water/MeOH/acetonitrile one can obtain confirmatory evidence of the identity of the suspect explosive.

Figure 2:
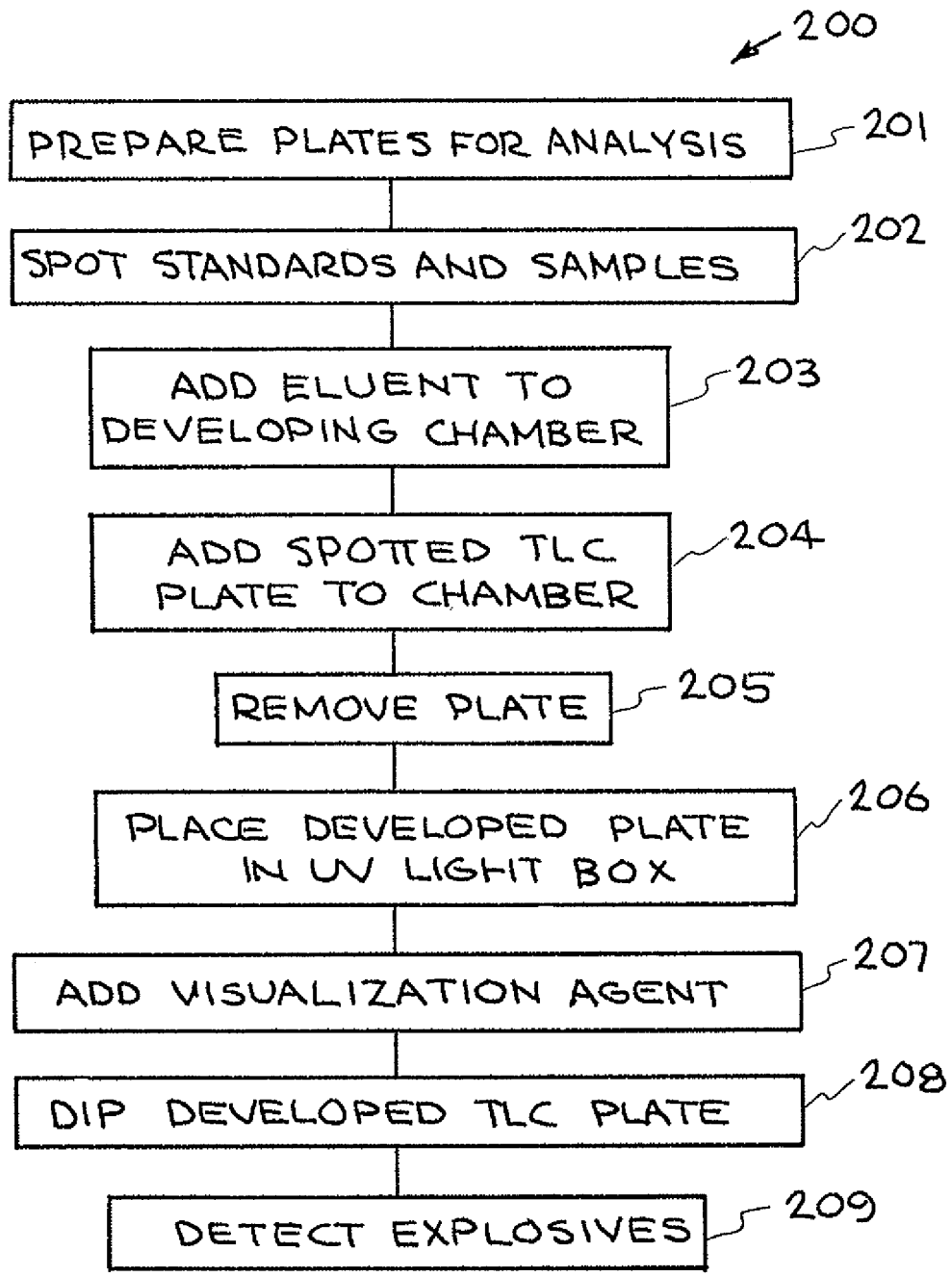
FIG. 2 illustrates an embodiment of a separation and detection method that allows reproducible separation and identification of explosives.

Referring now to FIG. 2, one embodiment of Applicants' invention provides a C18 TLC separation method that allows reproducible separation and identification of explosives. The system illustrated in FIG. 2 is designated generally by the reference numeral 200. The system 200 provides the separation and identification of both common military explosives (HMX, RDX, Tetryl, Explosive D, picric acid, CL-20, TNT, NG, and PETN) and the peroxide explosives, TATP and HMTD, using a single TLC plate and a single colorimetric reagent. The system illustrated in FIG. 2 includes the following steps.

Step 1—Prepare Plates for Analysis (Reference numeral 201)—To prepare plates for analysis, mark the spots on which to deposit the samples by touching the plate with a pencil, approximately 1 cm from the bottom of the plate. Be sure to mark spots for the samples beginning approximately 1 cm from the left and right edges of the TLC plates. 8 or 9 spots can fit across the plate. The standards can be located anywhere on the plate, but preferably toward the center of the plate.

Step 2—Spot Standards & Samples (Reference numeral 202)—Spot 1 μL of Standard 1 onto one spot and 1 μL of Standard 2 onto another spot. The remaining locations will be used for sample testing. Deposit unknowns in 1 μL aliquots on separate spots. Note that repetitive 1 μL additions can be made to the same spot as long as each application is allowed to dry completely before the next application (approximately 30 seconds).

Step 3—Add Eluent to Developing Chamber (Reference numeral 203)—Pipet 10 mL of the desired eluent [toluene:propan-2-ol (16:1) is the standard eluent; water:methanol:acetonitrile (11:9:2) is the secondary eluent)] into the developing chamber.

Step 4—Add Spotted TLC Plate to Chamber (Reference Numeral 204)—Add the spotted TLC plate to the chamber, and dose the chamber lid. Allow the RP plates to develop for either 14 min (Toluene:propan-2-ol (16:1) eluent) or 35 min (Methanol:Water:Acetonitrile (11:9:2) solvent system).

Step 5—Remove Plate (Reference numeral 205)—Remove plate and immediately draw a line across the top of the solvent front, and allow solvent to evaporate. It takes about 5 minutes for complete evaporation.

Step 6—Place Developed Plate in UV light Box (Reference numeral 206)—Place the developed plate in the UV light box and illuminate with the UV lamp (254 nm). If the solvent has not completely evaporated, the plate will appear dark; however, once the solvent has evaporated the plate is light blue under UV light. While irradiating the plate with UV light, photograph the explosives that are observed. At this point, 7 (Exp D, HMX, Tetryl, CL-20, picric acid, RDX, and TNT) of the explosives are identifiable due to their UV absorption.

Step 7—Add Visualization Agent (Reference numeral 207)—At this point the nitrate esters, PETN and NG, as well as TATP and HMTD are not visible because they are not UV active. In order to observe NG, PETN, TATP, and HMTD a visualization agent must be used. Fill a dip tank with approximately 50 mL of 0.02% diphenylbenzidine in ethanol. The tank should be approximately two-thirds full.

Step 8—Dip Developed TLC Plate (Reference numeral 207)—Dip the developed TLC plate (it is important that the plate be completely dry) into the solvent holding on to the top of the plate and making sure that the visualizing agent covers the plate above the solvent front line. Remove the plate quickly, lay it flat and allow the solvent to evaporate.

Step 9—Detect Explosives (Reference numeral 209)—Now TATP and HMTD (as well as CL-20) should be visible to the naked eye. A photograph can be obtained using the light box. After several minutes of UV irradiation, PETN and NG should be visible under both visible and the UV light. Diphenylbenzidine does not mask the explosives that are visible under UV light. When the reverse phase plate is run in the alternative solvent system notice that the elution of the explosives has completely changed.

The present invention provides a new field portable thin-layer chromatography (TLC) system for the detection and identification of common military, peroxide and commercial-type fuel/oxidizer explosives. The present invention provides a new methodology for the separation and identification of both common military explosives (HMX, RDX, Tetryl, Explosive D, picric acid, CL-20, TNT, NG, and PETN) and the peroxide explosives, TATP and HMTD, using a single TLC plate and a single calorimetric reagent. The new methodology employs reverse phase C18 TLC plates (RP-18). The RP-18 TLC plates gives better separation of the various explosives tested than the normal phase silica plates and have the advantage of by changing the elution solvent a reversal of the retention times of the various explosives could be achieved using the same plate. A single colorimetric reagent, 0.02% diphenylbenzidine in EtOH, was also found to be applicable to all the common military explosives tested along with the peroxide explosives, TATP and HMTD.

A detailed protocol was developed for Applicants' new C18 TLC separation methodology that allows reproducible separation and identification of the explosive standards. It involved spotting explosive unknowns and authentic samples onto the C18 TLC plate and developing the TLC plate with a 16:1 toluene/propan-2-ol mixture (takes around 15 minutes). The plate is dried and exposed to 254 nm UV light. The nitroaromatic and nitramine explosives show up as dark spots on a greenish background. The plate is then dipped into the 0.02% diphenylbenzidine/EtOH solution. After removing the plate and drying, TATP and HMTD show up as blue spots. The plate is then irradiated with 254 nm UV light for a few minutes and the nitrate esters show up as dark spots on a light blue background. This procedure not only identifies all the explosives mentioned but it also allows the user to separate the suspected compounds by their explosive class, i.e. nitramines, nitroaromatic, peroxides or nitrate esters. A different elution solvent may also be used with this plate. When a water/MeOH/acetonitrile solvent mixture is used as the eluant the explosives reverse their order of $R_f$ and Explosive D now has the highest $R_f$ value. By using these two elution solvents, 16:1 toluene/propan-2-ol and a 11:9:2 water/MeOH/acetonitrile one can obtain confirmatory evidence of the identity of the suspect explosive.

Applicants" procedures for the separation of the standard military explosives and peroxide explosives are described below:

For standard explosives: TNT, PSTN, NG, Picric Acid, Explosive D, Tetryl, HMX, RDX, TATP, HMTD and CL-20

Materials:

TLC plates: Machery-Nagel RP-18W $UV_{254}$, 10×10 cm plates (reverse phase (RP) plates)

Developing Solvents: Toluene:propan-2-ol (16:1)
Water:Methanol:Acetonitrile (11:9:2)
Visualization Agent: 0.02% diphenylbenzidine in ethanol
Explosive Standards: TNT, PETN, NG, Picric Acid, Explosive D, Tetryl, HMX, TATP, HMTD, CL-20 and RDX
254 nm UV lamp
Developing Tank
Dip Tank
Micropipette and tips Method:

The explosive standards are currently at a concentration of 250 ng/µL in acetonitrile except as noted. Standard 1 contains the following explosives: TNT, NG, RDX, Picric Acid, and HMTD (0.02 mg/mL) Standard 2 contains PETN, Tetryl, HMX, CL-20, Explosive D and TATP (0.05 mg/mL).

To prepare plates for analysis, mark the spots on which to deposit the samples by touching the plate with a pencil, approximately 1 cm from the bottom of the plate. Be sure to mark spots for the samples beginning approximately 1 cm from the left and right edges of the TLC plates. 8 or 9 spots can fit across the plate. The standards can be located anywhere on the plate, but preferably toward the center of the plate. Spot 1 µL of Standard 1 onto one spot and 1 µL of Standard 2 onto another spot. The remaining locations will be used for sample testing. Deposit unknowns in 1 uL aliquots on separate spots. Note that repetitive 1 µL additions can be made to the same spot as long as each application is allowed to dry completely before the next application (approximately 30 seconds).

Pipet 10 mL of the desired eluent [toluene:propan-2-ol (16:1) is the standard eluent; water:methanol:acetonitrile (11:9:2) is the secondary eluent)] into the developing chamber, add the spotted TLC plate to the chamber, and close the chamber lid. Allow the RP plates to develop for either 14 min (Toluene:propan-2-ol (16:1) eluent) or 35 min (Methanol:Water:Acetonitrile (11:9:2) solvent system). Remove plate and immediately draw a line across the top of the solvent front, and allow solvent to evaporate. It takes about 5 minutes for complete evaporation. Place the developed plate in the UV light box and illuminate with the UV lamp (254 nm). If the solvent has not completely evaporated, the plate will appear dark; however, once the solvent has evaporated the plate is light blue under UV light. While irradiating the plate with UV light, photograph the explosives that are observed. At this point, 7 (Exp D, HMX, Tetryl, CL-20, picric acid, RDX, and TNT) of the explosives are identifiable due to their UV absorption.

At this point the nitrate esters, PETN and NG, as well as TATP and HMTD are not visible because they are not UV active. In order to observe NG, PETN, TATP, and HMTD a visualization agent must be used. Fill a dip tank with approximately 50 mL of 0.02% diphenylbenzidine in ethanol. The tank should be approximately two-thirds full. Dip the developed TLC plate (it is important that the plate be completely dry) into the solvent holding on to the top of the plate and making sure that the visualizing agent covers the plate above the solvent front line. Remove the plate quickly, lay it flat and allow the solvent to evaporate. Now TATP and HMTD (as well as CL-20) should be visible to the naked eye. A photograph can be obtained using the light box. After several minutes of UV irradiation, PETN and NG should be visible under both visible and the UV light. Diphenylbenzidine does not mask the explosives that are visible under UV light. When the reverse phase plate is run in the alternative solvent system notice that the elution of the explosives has completely changed.

It was not possible in any of these solvent systems to separate picric acid from Exp D. Table 1 shows the $R_f$ values of the listed explosives. Only the reverse phase plate in the Toluene:propan-2-ol (16:1) solvent system gives complete separation of the remaining explosives.

TABLE 1

| | $R_f$ values | |
|---|---|---|
| explosive | RP plate* | RP plate** |
| picric acid | 0.09 | 0.76 |
| Exp D | 0.09 | 0.76 |
| HMX | 0.31 | 0.41 |
| RDX | 0.39 | 0.44 |
| Tetryl | 0.61 | 0.16 |
| NG | 0.73 | 0.28 |
| HMTD | 0.43 | 0.63 |
| TATP | 0.45 | 0.36 |
| CL-20 | 0.28 | 0.01 |
| PETN | 0.78 | 0.08 |
| TNT | 0.86 | 0.23 |

*Toluene: propan-2-ol eluent
**Water:Methanol:Acetonitrile eluent

TABLE 2

| | Visualization | | | |
|---|---|---|---|---|
| explosive | UV | DPB* | DPB + UV | detection limit (ng) |
| picric acid | + | | + | 25 |
| Exp D | + | | + | 25 |
| HMX | + | | + | 50 |
| RDX | + | | + | 50 |
| Tetryl | + | | + | 50 |
| NG | | | + | 100 |
| HMTD | | + | + | 10 |
| CL-20 | + | + | + | 50 |
| TATP | | + | + | 25 |
| PETN | | | + | 100 |
| TNT | + | | + | 100 |

*0.02% Diphenylbenzidine

A methodology for the separation of various inorganic oxidizers used in commonly reported fuel/oxidizer explosives by TLC combined with calorimetric determination of the suspect anions was developed. Applicants' methodology uses EMD Chemicals HPTLC cellulose plates and 0.1% sodium 2,6-dichloroindophenol hydrate as the calorimetric reagent. It allows the separation and identification of the inorganic oxidizers, nitrate, nitrite, perchlorate, chlorate and bromate. Several different solvent systems were tested and the one that gave the best separation was a n-BuOH:acetone:$NH_4OH$ (3:3:2) mixture. The expected $R_f$ values for a variety of solvent systems tested are listed below.

Materials:

TLC plates: EMD Chemicals Inc., HPTLC cellulose, 10×10 cm plates

Developing Solvents: 1-Butanol:Acetone:Ammonia (3:3:2)

Visualization Solvents: 0.1% Sodium 2,6-dichloroindophenol hydrate in acetone

Ion Standards Ammonium perchlorate, sodium nitrite, ammonium nitrate, sodium chlorate, and sodium bromate in water Developing Tank
Dip Tank
Micropipette and tips
Method:

The explosive standards are currently at a concentration of 10 µg/µL in water in individual vials.

Using a clear ruler with metric markings, the TLC plate is prepared for development by marking along a straight edge 1 cm from the bottom. Then starting approximately 1.5 cm from the left mark 10 or 11 spots 1 cm apart and ending at least 1 cm from the right edge of the TLC plates. Each spot should be marked with an identifying reference mark to identify the sample or standard associated with that spot. This may be applied with a pencil either at the very top of the plate or at the very bottom of the plate below the solvent line. Deposit 0.2 µL of each of the 5 standards on its own spot. This leaves 5 to 6 spots to be used for sample testing. The spots should be completely dry before placing in the developing tank. Blowing lightly on the spot as you apply the standards and unknowns will aid the drying.

Add the developing solution to the developing chamber. Add 7.5 mL of a 1:1 mixture of n-butanol:acetone to the chamber. Then add 2.5 mL of conc. $NH_4OH$ (28% aqueous $NH_4OH$). Close the lid and mix by moving the chamber sideways being careful not to slosh the eluent out of the tank. Add the spotted TLC plate to the chamber and close the chamber lid. The level of the eluent must remain below the line on which the spots were applied. Allow plate to develop for 35 minutes (do not allow the solvent front to go all the way to the top of the plate). Remove plate and immediately draw a line across the top of the solvent front, and allow the solvent to evaporate (~5 min). The plate should not smell of ammonia at this point. Dip the dried plate in a solution of 0.1% 2,6-dichloroindophenol in acetone. Remove it immediately and let the excess drain back into the tank. Lay flat to dry (takes less than 30 sec). You should immediately see an elution pattern that looks like the photo below. Note that the $Na^+$ and $NH_4^+$ cations are also visible and differentiateable by their color. Also note that nitrite is distinguishable from perchlorate, nitrate, chlorate, and bromate by its blue color. The expected $R_f$ values for a variety of solvent systems are listed in Table 3 below. The n-BuOH:acetone:$NH_4OH$ (3:3:2) solvent system (in red) goves the most clear separation of the ions. The $R_f$ of a spot is calculated by measuring the distance to the bottom of the spot to be analyzed. This distance divided by the measured distance to the solvent front gives the $R_f$ value.

18W plates) as the adsorbent medium and 0.5% dimethylaminobenzaldehyde (DMBA) in ethanol containing 0.5% sulfuric acid as the calorimetric reagent. Urea nitrate is separated by the TLC plate into its components, urea and nitric acid and the urea is detected by the calorimetric reagent. The $R_f$ value for urea on RP plates is 0.6. The sensitivity is 500 ng for urea nitrate and 200 ng for urea.

Materials:
TLC plates: Machery-Nagel RP-18W $UV_{254}$, 10×10 cm plates (reverse phase (RP) plates
Developing Solvent Ethanol:Ammonium hydroxide (99:1)
Visualization: 0.5% dimethylaminobenzaldehyde (DMBA) in ethanol containing 0.5% sulfuric acid (See Table 2)
Standards: urea and urea nitrate in ethanol at a concentration of 1.0 mg/mL
Method:

With a pencil mark the plates approximately 1 cm from the bottom of the plate. Mark 9 or 10 spots across the bottom starting about 1 cm from the left or right edges of the plate. Aliquots (0.2 uL to 4×0.5 uL) are spotted on the plate using a pipet and plastic tips. After each application the spot is allowed to dry before further applications. Two lanes should be devoted to standards leaving 7 or 8 for unknowns.

Add the freshly prepared developing solution to the developing chamber. Insert the plate into the chamber and immediately close the lid. Allow the plate to develop for 30 min. After that time remove the plate and immediately draw a line across the solvent front. Allow the solvent to evaporate (~5 min). The plate should not smell of ammonia at this point. Dip the dried plate in the DMBA visualization solution. Remove the plate immediately from the dip tank and allow extra fluid to drain back into the tank. Lay flat to dry. After drying the plate should look like the photo below. The $R_f$ value for urea on RP plates is 0.6. The sensitivity is 500 ng for urea nitrate and 200 ng for urea.

The transportation and storage of flammable liquids as commercial products are generally more difficult and require more regulation than flammable solids or gels. Applicants' TLC systems all use flammable liquids as the developing solvents. This may become an issue in the future when Applicants' systems become commercial products. To address this issue we investigated the use of gelling agents that would convert the solvent systems to "gels" instead of liquids. We found that treatment of the developing solvent with Cab-O-Sil, an inexpensive commercially available thixotropic gel-

TABLE 3

| solvent system | $R_f$ | | | | |
| --- | --- | --- | --- | --- | --- |
| | perchlorate | nitrite | nitrate | chlorate | bromate |
| iPrOH:acetone:NH$_4$OH:H$_2$O (30:40:30:5) | 0.90 | 0.64 | 0.74 | 0.79 | 0.60 |
| acetone:NH$_4$OH (2:1) | 0.97 | 0.71 | 0.80 | 0.86 | 0.68 |
| MeOH:NH$_4$OH (2:1) | 0.82 | 0.77 | 0.76 | 0.80 | 0.74 |
| nBuOH:NH$_4$OH (2:1) | 0.37 | 0.23 | 0.28 | 0.31 | 0.17 |
| nBuOH:acetone:NH$_4$OH:H$_2$O (30:40:30:5) | 0.77 | 0.58 | 0.64 | 0.70 | 0.53 |
| nBuOH:acetone:NH$_4$OH (1:1:1) | 0.71 | 0.52 | 0.59 | 0.63 | 0.48 |
| nBuOH:acetone:NH$_4$OH (3:3:2) | 0.68 | 0.41 | 0.51 | 0.55 | 0.36 |
| nBuOH:acetone:NH$_4$OH (2:2:1) | 0.73 | 0.36 | 0.49 | 0.55 | 0.31 |
| nBuOH:acetone:NH$_4$OH (5:5:2) | 0.65 | 0.24 | 0.39 | 0.46 | 0.20 |

TLC Method for Urea Detection:

A new methodology for the separation and identification of urea in urea nitrate-based explosives by thin-layer chromatography was developed. The methodology involved the use of Machery-Nagel RP-18W $UV_{254}$, 10×10 cm plates (RPling agent, yielded a thick gel that may be dispensed using a spatula or spoon or through a squeezable tube similar to a toothpaste tube. A 6.5% Cab-O-Sil/16:1 toleune/propan-2-ol mixture gel, when used as the developing medium, gave a comparable (though slightly diminished) separation of the suspect explosives to that of the neat liquid. The Cab-O-Sil gels were stable for weeks if stored in a tightly closed container.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A thin-layer chromatography method using a single thin-layer chromatography plate and a single colorimetric reagent for detection and identification of both military explosives and peroxide explosives in samples using the single thin-layer chromatography plate and using the single colorimetric reagent, consisting of the steps of:
providing a single reverse-phase thin-layer chromatography plate for detection and identification of both military explosives and peroxide explosives in samples;
preparing said single reverse-phase thin-layer chromatography plate for detection and identification of both military explosives and peroxide explosives in sample by marking spots on which to deposit the samples;
spotting one micro liter of a first standard onto one of said spots wherein said first standard is a standard for military explosives, spotting one micro liter of a second standard onto another of said spots wherein said second standard is a standard for peroxide explosives, and spotting samples onto other of said spots producing a spotted single reverse-phase thin-layer chromatography plate for detection and identification of both military explosives and peroxide explosives in sample;
adding eluent to a developing chamber;
adding said spotted single reverse-phase thin-layer chromatography plate to said developing chamber;
removing said spotted single reverse-phase thin-layer chromatography plate from said developing chamber producing a developed single reverse-phase thin-layer chromatography plate;
placing said developed single reverse-phase thin-layer chromatography plate in an ultraviolet light box;
adding a single colorimetric visualization reagent to a dip tank, wherein said single colorimetric visualization reagent is diphenylbenzidine in EtOH;
dipping said developed single reverse-phase thin-layer chromatography plate in said dip tank and remove said developed single reverse-phase thin-layer chromatography plate; and
detecting the military explosives and detecting the peroxide explosives by viewing said developed single reverse-phase thin-layer chromatography plate.

2. The thin-layer chromatography method for detection and identification of both military explosives and peroxide explosives in samples using a single thin-layer chromatography plate of claim 1 wherein said step of preparing said single reverse-phase thin-layer chromatography plate by marking spots on which to deposit the samples comprises touching said single reverse-phase thin-layer chromatography plate with a pencil to mark spots on which to deposit the samples.

3. The thin-layer chromatography method for detection and identification of both military explosives and peroxide explosives in samples using a single thin-layer chromatography plate of claim 1 wherein said step of spotting samples onto other of said spots producing a spotted single reverse-phase thin-layer chromatography plate comprises spotting one micro liter of one of said samples onto another of said spots and waiting for said one micro liter of one of said samples to dry before spotting another of said samples onto other of said spots.

4. The thin-layer chromatography method for detection and identification of both common military and peroxide explosives in samples using a single thin-layer chromatography plate of claim 1 wherein said step of adding eluent to a developing chamber comprises pipeting ten milliliter of toluene:propan-2-ol into said developing chamber.

5. The thin-layer chromatography method for detection and identification of both common military and peroxide explosives in samples using a single thin-layer chromatography plate of claim 1 wherein said step of adding eluent to a developing chamber comprises pipeting ten milliliter of water:methanol:acetonitrile into said developing chamber.

6. The thin-layer chromatography method for detection and identification of both common military and peroxide explosives in samples using a single thin-layer chromatography plate of claim 1 wherein said step of add said spotted single reverse-phase thin-layer chromatography plate to said developing chamber includes allowing said spotted single reverse-phase thin-layer chromatography plate to develop for between fourteen minutes and thirty-five minutes.

7. The thin-layer chromatography method for detection and identification of both common military and peroxide explosives in samples using a single thin-layer chromatography plate of claim 1 wherein said developing chamber contains solvent and wherein said step of removing said spotted single reverse-phase thin-layer chromatography plate from said developing chamber producing a developed single reverse-phase thin-layer chromatography plate includes allowing said solvent to evaporate.

8. The thin-layer chromatography method for detection and identification of both common military and peroxide explosives in samples using a single thin-layer chromatography plate of claim 1 wherein said developing chamber contains solvent and wherein said step of removing said spotted single reverse-phase thin-layer chromatography plate from said developing chamber producing a developed single reverse-phase thin-layer chromatography plate includes allowing said solvent to evaporate for five minutes.

9. The thin-layer chromatography method for detection and identification of both common military and peroxide explosives in samples using a single thin-layer chromatography plate of claim 1 wherein said step of placing said developed single reverse-phase thin-layer chromatography plate in an ultraviolet light box includes photographing said developed single reverse-phase thin-layer chromatography plate.

10. The thin-layer chromatography method for detection and identification of both common military and peroxide explosives in samples using a single thin-layer chromatography plate of claim 1 wherein said step of adding a visualization agent to a dip tank comprises adding fifty milliliters of two one hundredths of a percent diphenylbenzidine in ethanol to a dip tank.

11. The thin-layer chromatography method for detection and identification of both common military and peroxide explosives in samples using a single thin-layer chromatography plate of claim 1 wherein said step of detecting explosives by viewing said developed single reverse-phase thin-layer chromatography plate includes photographing said developed single reverse-phase thin-layer chromatography plate.

12. A thin-layer chromatography method using a single thin-layer chromatography plate and a single colorimetric reagent for detection and identification of both common military and peroxide explosives in samples using the single thin-layer chromatography plate and using the single colorimetric reagent, consisting of the steps of:

provided a single reverse-phase thin-layer chromatography plate for detection and identification of both military explosives and peroxide explosives in samples;

preparing said single reverse-phase thin-layer chromatography plate for detection and identification of both military explosives and peroxide explosives in sample by marking spots on which to deposit the samples by touching said single reverse-phase thin-layer chromatography plate with a marker;

spotting one micro liter of a first standard onto one of said spots wherein said first standard is a standard for military explosives, spotting one micro liter of a second standard onto another of said spots wherein said second standard is a standard for peroxide explosives, and spotting samples onto other of said spots producing a spotted single reverse-phase thin-layer chromatography plate for detection and identification of both military explosives and peroxide explosives in sample;

adding eluent to a developing chamber;

add said spotted single reverse-phase thin-layer chromatography plate to said developing chamber;

removing said spotted single reverse-phase thin-layer chromatography plate from said developing chamber producing a developed single reverse-phase thin-layer chromatography plate;

placing said developed single reverse-phase thin-layer chromatography plate in an ultraviolet light box;

adding a single colorimetric visualization reagent to a dip tank;

dipping said developed single reverse-phase thin-layer chromatography plate in said dip tank and remove said developed single reverse-phase thin-layer chromatography plate quickly; and detecting the military explosives and detecting the peroxide explosives by viewing said developed single reverse-phase thin-layer chromatography plate.

13. The thin-layer chromatography method for detection and identification of both common military and peroxide explosives in samples using a single thin-layer chromatograph plate of claim 12 wherein said step of preparing said single reverse-phase thin-layer chromatography plate by marking spots on which to deposit the samples by touching said single reverse-phase thin-layer chromatography plate with a marker comprises touching said single reverse-phase thin-layer chromatography plate with a pencil.

14. The thin-layer chromatography method for detection and identification of both common military and peroxide explosives in samples using a single thin-layer chromatograph plate of claim 12 wherein said step of spotting samples onto other of said spots producing a spotted single reverse-phase thin-layer chromatography plate comprises spotting one micro liter of one of said samples onto another of said spots and waiting for said one micro liter of one of said samples to dry before spotting another of said samples onto other of said spots.

15. The thin-layer chromatography method for detection and identification of both common military and peroxide explosives in samples using a single thin-layer chromatograph plate of claim 14 wherein said step of spotting samples onto other of said spots producing a spotted single reverse-phase thin-layer chromatography plate comprises spotting one micro liter of one of said samples onto another of said spots and waiting for said one micro liter of one of said samples to dry before spotting another of said samples onto other of said spots and repeating said step of spotting one micro liter of one of said samples onto another of said spots and waiting for said one micro liter of one of said samples to dry before spotting another of said samples onto other of said spots.

16. The thin-layer chromatography method for detection and identification of both common military and peroxide explosives in samples using a single thin-layer chromatograph plate of claim 12 wherein said step of adding eluent to a developing chamber comprises pipeting ten milliliter of toluene:propan-2-ol into said developing chamber.

17. The thin-layer chromatography method for detection and identification of both common military and peroxide explosives in samples using a single thin-layer chromatograph plate of claim 12 wherein said step of adding eluent to a developing chamber comprises pipeting ten milliliter of water:methanol:acetonitrile into said developing chamber.

18. The thin-layer chromatography method for detection and identification of both common military and peroxide explosives in samples using a single thin-layer chromatograph plate of claim 12 wherein said step of adding said spotted single reverse-phase thin-layer chromatography plate to said developing chamber includes allowing said spotted single reverse-phase thin-layer chromatography plate to develop for between fourteen minutes and thirty-five minutes.

19. The thin-layer chromatography method for detection and identification of both common military and peroxide explosives in samples using a single thin-layer chromatograph plate of claim 12 wherein said developing chamber contains solvent and wherein said step of removing said spotted single reverse-phase thin-layer chromatography plate from said developing chamber producing a developed single reverse-phase thin-layer chromatography plate includes allowing said solvent to evaporate.

20. The thin-layer chromatography method for detection and identification of both common military and peroxide explosives in samples using a single thin-layer chromatograph plate of claim 12 wherein said developing chamber contains solvent and wherein said step of removing said spotted single reverse-phase thin-layer chromatography plate from said developing chamber producing a developed single reverse-phase thin-layer chromatography plate includes allowing said solvent to evaporate for five minutes.

21. The thin-layer chromatography method for detection and identification of both common military and peroxide explosives in samples using a single thin-layer chromatograph plate of claim 12 wherein said step of placing said developed single reverse-phase thin-layer chromatography plate in an ultraviolet light box includes photographing said developed single reverse-phase thin-layer chromatography plate.

22. The thin-layer chromatography method for detection and identification of both common military and peroxide explosives in samples using a single thin-layer chromatograph plate of claim 12 wherein said step of adding a visualization agent to a dip tank comprises adding fifty milliliters of two one hundredths of a percent diphenylbenzidine in ethanol to a dip tank.

23. The thin-layer chromatography method for detection and identification of both common military and peroxide explosives in samples using a single thin-layer chromatograph plate of claim 12 wherein said step of detecting explosives by viewing said developed plate includes photographing said developed single reverse-phase thin-layer chromatography plate.

* * * * *